United States Patent [19]
Katz et al.

[11] Patent Number: 5,716,614
[45] Date of Patent: Feb. 10, 1998

[54] METHOD FOR DELIVERING ACTIVE AGENTS TO MAMMALIAN BRAINS IN A COMPLEX WITH EICOSAPENTAENOIC ACID OR DOCOSAHEXAENOIC ACID-CONJUGATED POLYCATIONIC CARRIER

[75] Inventors: Robert Katz, Gaithersburg; Maria Tomoaia-Cotisel, Rockville, both of Md.

[73] Assignee: Molecular/Structural BioTechnologies, Inc., Bethesda, Md.

[21] Appl. No.: 286,327

[22] Filed: Aug. 5, 1994

[51] Int. Cl.⁶ .................. A61K 38/54; A61K 39/395; A61K 45/00; A61K 38/00
[52] U.S. Cl. .................. 424/94.3; 424/130.1; 424/283.1; 514/2
[58] Field of Search .................. 424/130.1, 283.1, 424/94.3; 514/2

[56] References Cited

U.S. PATENT DOCUMENTS

| | | | |
|---|---|---|---|
| 4,479,940 | 10/1984 | Bizzini | 514/773 |
| 4,921,705 | 5/1990 | Arai et al. | 424/450 |
| 4,933,324 | 6/1990 | Shashoua | 514/17 |
| 4,937,262 | 6/1990 | Davidson | 514/492 |
| 4,939,174 | 7/1990 | Shashoua | 514/549 |
| 4,963,368 | 10/1990 | Antrim et al. | 424/498 |
| 4,970,076 | 11/1990 | Horrobin | 424/456 |
| 5,093,317 | 3/1992 | Lewis et al. | 514/12 |

FOREIGN PATENT DOCUMENTS

92/20362  11/1992  WIPO .

OTHER PUBLICATIONS

Shashoua, WO 9220362, "Nerve Growth Peptides Derived from Ependymin and Their Uses", *Chem. Abstr.* 119, Abstract No. 152847.

*Primary Examiner*—Jon P. Weber
*Attorney, Agent, or Firm*—Isaac A. Angres

[57] ABSTRACT

A method is disclosed for delivering biologically active agents to a mammalian brain by administering a complex of the biologically active agent with a polycationic carrier coupled to 2–20 eicosapentaenoic acid or docosahexaenoic acid moieties and additional eicosapentaenoic acid or docosahexaenoic acid moieties. The polycationic carrier is poly-lysine, poly-arginine or poly-ornithine of 5–50 amino acid residues. The addition of a targeting moiety selected from tetanus toxin C fragrant, α-bungarotoxin and nerve growth factor to the complex facilitates delivery of the biologically active agent to glial tissue, or to cortical, cholinergic and adrenergic neurons.

17 Claims, 7 Drawing Sheets

```
                  _____
                  Lipophilic moiety
                       (LP)
                  _____
                         |
                covalent linkage
                via peptide bond
                         |
                 [NH-CH-CO-]ₙ- covalent linkage --[NH-CH-CO]ₘ-
                         \                                \
                         /                                /
                         \                                \
                         /                                /
                         NH                               NH
                         |                                |
                 covalent linkage              covalent linkage
                 to agent                      to targeting moiety

|                                |

_____          _____
                 Hydrophilic agent (A)         Tetanus toxin fragment C
                    (enzyme, E)                TTC as a targeting moiety
                 _____          _____
```

Figure 3

METHOD FOR DELIVERING ACTIVE AGENTS TO MAMMALIAN BRAINS IN A COMPLEX WITH EICOSAPENTAENOIC ACID OR DOCOSAHEXAENOIC ACID-CONJUGATED POLYCATIONIC CARRIER

FIELD OF THE INVENTION

The present invention relates to site-specific biomolecular lipophilic complexes, also called conjugates or transport vectors. These complexes comprise an omega-3 fatty acid and derivatives thereof, and a therapeutic, prophylactic, diagnostic or a research agent. Further, said complex is conjugated with cationic macromolecular carriers to enhance its passage from the blood circulation to the brain. The resultant conjugates are specific for sustained release delivery of said agents to the central nervous system (CNS), particularly to the neurons of the cerebral cortex and corpus striatum (e.g., cholinergic and adrenergic neurons) and to the glial tissue (neuroglial cells, including, astrocytes and macroglial cells) in animals and humans. In addition, targeting moieties such as neurotoxins and fragments thereof are added to said complex to facilitate its uptake by the target brain cells.

Also, disclosed are pharmaceutical compositions containing poly-unsaturated site-specific complexes/conjugates for the treatment of a wide variety of diseases relating to severe deterioration of the central nervous system, e.g., dementias, neurodegenerative disorders, neurological diseases, malignant brain tumors, inborn errors of metabolism (i.e., lysosomal storage disorders), and the like.

The specification and claims that follow cite numerous patents and publications and their content whether for background or experimental purposes are incorporated by reference herein.

BACKGROUND

During the last two decades, various agent delivery systems have been designed by using carriers such as proteins, peptides, polysaccharides, synthetic polymers, colloidal particles (i.e., liposomes, vesicles or micelles), microemulsions, microspheres and nanoparticles. These carriers contain entrapped pharmaceutically useful agents to achieve a controlled cell-specific or tissue-specific drug release.

Further efforts and research are being directed to develop and design novel systems of specific delivery to a target cell or tissue for the agents that cross biological barriers at relatively low rates. The purpose of the present invention is to delineate a method that improves the transport to a desired location and delivery characteristics of an agent molecule, thus increasing its bioavailability.

The term "agent" as used herein relates to therapeutic, prophylactic and diagnostic compounds. These compounds are biologically active with beneficial effects in both animals and humans. Agents include lysosomal enzymes such as ceramidase, glucocerebrosidase, beta-galactosidase, beta-hexosaminidase A, beta-hexosaminidase A & B, galactosylceramidase, arylsulfatase A, sphingomyelinase, alpha-galactosidase B, aspartylglycosaminidase, alpha-L-fucosidase, iduronate sulfatase, alpha-L-iduronidase, glcNAc-6-sulfatase and beta-glucuronidase. Also included are serum proteins namely immunoglobulins, interleukins, interferons, hormones, such as insulin, parathyroid hormone, pigmentary hormone, thyroid-stimulating hormones, tissue plasminogen activator, nerve growth factors, nucleic acids and derivatives thereof, nucleotides, oligonucleotides, antisense oligonucleotide analogs, genes, transfected cells, biological vectors, cloning vectors and expression vectors. Toxins or their non-toxic fragments, diagnostic and research reagents are also included.

Agents must reach brain cells and tissue to exert desired therapeutic or prophylactic effects. Intravenous administration will require their passage from the blood to the brain by crossing the microcapillary membranes of the cerebrovascular endothelium also called the blood-brain barrier or BBB). Various BBB-crossing enhancers have been identified (e.g., permeabilizer peptides).

There are also methods to circumvent the BBB. These include intrathecal administration of agents directly into the cerebrospinal fluid (CSF), or therein through surgical implants, or still directly to the brain by infusion into the interstitial brain tissue. All of these drug delivery approaches that relate to this invention are described in detail and referenced below.

The blood-brain barrier (BBB) is formed by cerebral endothelial cells under the influence of astroglial cells of the brain [Johansson, Progress in Brain Research, 91: 171–175 (1992); Ermisch, Progress in Brain Research, 91: 155–161 (1992); Schlosshauer, BioEssays, 15(5): 341–346 (1993)]. Briefly, the BBB contains a monolayer of tightly connected microvascular endothelial cells with anionic charges. This layer separates two fluid-containing compartments: the blood plasma (BP) and extracellular fluid (ECF) of the brain parenchyma. One of the main functions of the BBB is to regulate the transfer of components between BP and ECF. The BBB limits free passage of the agent molecules from the blood to the brain cells. This limited penetration into the CNS is noticeable with large molecules of high polarity such as protein conjugates, enzymes, growth factors, genetic vectors as reported by Bobo et al., Proc. Natl. Acad. Sci. USA, 91: 2076–2080 (1994). Poor agent delivery to the CNS limits the application of basic and promising findings for the treatment of neurodegenerative disorders and neurological diseases.

Several techniques are used to deliver therapeutic agents selectively to the brain, circumventing the BBB through intrathecal injections, surgical implants and interstitial infusion [as reported by Ommaya, Cancer Drug Delivery, 1(2): 169–178 (1984) and U.S. Pat. No. 5,222,982, and by Bobo et al., Proc. Natl. Acad. Sci. USA, 91: 2076–2080 (1994)]. This strategy uses delivery of the agent to the CNS by direct administration into the cerebrospinal fluid (CSF) or into the brain parenchyma (ECF). Within this strategy, the findings show that the agent penetration from CSF or ECF into the brain is extremely limited, particularly for agents of high molecular weight. Other methods of administration such as oral delivery of therapeutic agents is also within the scope of this invention.

One of the objectives of the present invention is to design and synthesize new vehicles, called also complexes or conjugates, for macromolecular agents such as enzymes or proteins, to increase their transport properties and the rate of distribution of said agent through the brain relative to its tissue clearance. The novel site-specific complexes of this invention improve the transport and penetration properties of the agent. For example, the enzyme, as an agent and part of a site-specific complex containing an omega-3 fatty acid and derivatives thereof, can selectively reach the brain tissue and the entire affected brain could be treated.

Another strategy to improve agent delivery to the CNS is by increasing the agent absorption (adsorption and transport) through the BBB and their uptake by the cells [Broadwell, Acta Neuropathol., 79: 117–128 (1989); Pardridge et al., J.

Pharmacol. Experim. Therapeutics, 255(2): 893–899 (1990); Banks et al., Progress in Brain Research, 91: 139–148 (1992); Pardridge, Fuel Homeostasis and the Nervous System, Edited by Vranic et al., Plenum Press, New York, 43–53 (1991)]. Within this strategy, the passage of agents through the BBB to the brain can be enhanced by altering either the permeability of the agent itself or the characteristics of the BBB. Thus, the passage of the agent can be facilitated by increasing its lipid solubility through chemical modification of the agent itself, and/or by its coupling to a cationic carrier, or still by its covalent coupling to a peptide vector capable of transporting the agent through the BBB. Peptide transport vectors are also known as BBB permeabilizer compounds [U.S. Pat. No. 5,268,164].

Another major objective of this invention is to design a targeting carrier macromolecule with lipophilic properties. The resultant conjugate or complex comprising an agent, a lipophilic carrier and a site-specific moiety, is targeted to specific cells in the brain. The lipophilic moiety is either eicosapentanoic acid (EPA) or docosahexaenoic acid (DHA) or derivatives thereof (e.g., N-eicosapentaenoyl amino ethanol, N-docosahexaenoyl amino ethanol, and lipids). EPA and its derivatives will direct the agent to the glia while DHA and its derivatives will direct the agent to cortical, cholinergic and adrenergic neurons. The use of lipophilic moieties could further protect the agent from enzymatic degradation during its passage across the BBB.

There is a significant unidirectional transport of polyunsaturated fatty acids of the omega-3 series (PUFA, omega-3) across the BBB that is possibly mediated by a specific transporter and/or a receptor or simply by the transcytosis process. Prior art discloses that BBB can target the release of omega-3 fatty acids into the brain and thus aids in the enrichment of these essential fatty acids observed in the brain [Yerram et al., J. Lipid Research, 30: 1747–1757 (1989); Moore et al., J. Neurochem., 55(2): 391–402 (1990); Moore et al. J. Neurochem., 56 (2):518–524 (1991)]. Also, prior art indicates that BBB and astrocytes, and not neurons, are responsible for the elongation and desaturation of eicosapentaenoic acid in the rodent brain. Moreover, astrocytes are apparently responsible for the local synthesis of docosahexaenoic acid (symbolized by DHA or C22:6, omega-3) and the release of the latter into the brain tissue as well as its subsequent transfer to neurons. If the DHA is synthesised in the liver or administered directly in BP, then it apparently crosses freely the BBB to the brain. Therefore, the DHA enrichment in the brain may result from two important roles of BBB: (1) to target and to release DHA to the brain and (2) to block its egress from the brain.

Prior art shows, for example, conjugates of proteins with water soluble polymers which have been manufactured and used for pharmaceutical purposes. U.S. Pat. No. 4,935,465 teaches the attachment of one or more polymer molecules to a protein. However, attachment of polymers to proteins, particularly to enzymes which act on low molecular weight substrates, retards enzyme clearance and decreases enzyme antigenicity. When the enzyme acts on a macromolecular substrate or on a cell-bound substrate, the enzyme activity of the conjugate could be diminished.

Other examples [U.S. Pat. No. 4,701,521, and U.S. Pat. No. 4,847,240] describe a method of covalently bonding an agent to cationic macromolecular carrier which enters into the cells relatively higher rates. These patents teach enhancement cellular uptake of bio-molecules into the cells when covalently bonded to cationic resins.

U.S. Pat. No. 4,046,722 discloses anti-cancer drugs covalently bonded to cationic polymers for the purpose of directing them to cells bearing specific antigens. The polymeric carriers have molecular weights of about 5,000 to 500,000.

Further work involving covalent bonding of an agent to a cationic polymer through an acidity-sensitive intermediate (called also spacer) molecule, is described in U.S. Pat. No. 4,631,190 and U.S. Pat. No. 5,144,011. Various spacer molecules, such as cisaconitic acid, are covalently linked to the agent and to the polymeric carrier. They control the release of the agent from the macromolecular carrier when subjected to a mild increase in acidity, such as probably occurs within a lysosome of the cell. The drug can be selectively hydrolyzed from the molecular conjugate and released in the cell in its unmodified and active form. Molecular conjugates are transported to lysosomes, where they are metabolised under the action of lysosomal enzymes at a substantially more acidic pH than other compartments or fluids within a cell or body. The pH of a lysosome is shown to be about 4.8, while during the initial stage of the conjugate digestion is possibly 3.8.

U.S. Pat. No. 5,308,701 discloses a method for encapsulating proteins within a synthetic cationic poly-L-lysine, crosslinked with multivalent ions of the opposite charge, to form a hydrolytically stable gel.

In general, both natural and synthetic polymers have been used as drug carriers. Synthetic polymers are more suitable as drug carriers because their structure can be systematically altered in a defined way and, in turn, it is possible to elucidate biological experiments and to overcome problems related to the application of macromolecular drug conjugates in human medicine and particularly to deliver enzyme-conjugates to neurons.

In the present invention, the polymeric carrier system comprises poly-L-lysine (PLL). PLL is a bio-compatible, hydrophilic polymer with very thoroughly studied chemical and biological properties. Other cationic poly amino acids such as poly-arginine and poly-ornithine are within the scope of this invention.

The prior art is silent on lipophilic macromolecular conjugates, like a targeting lipophilic macromolecular vehicle, for therapeutic or diagnostic use. The novel site-specific lipophilic vehicles of this invention are employed to deliver therapeutic agents selectively to the CNS, using polypeptides as macromolecular carriers covalently bound with functional amphipathic molecules, such as fatty acids, phospholipids, etc. Also, short peptides are disclosed to provide "spacers" between the components of the vehicle as shown in the description of the preferred embodiments.

Alternatively, enzyme molecules are attached directly to poly-unsaturated lipophilic moieties. One or more fatty acyl moieties can be attached to the enzyme by reacting an imidate activated enzyme with, for example, docosahexaenoic acid. The number of attached moieties is limited only by the number of available —$NH_2$ groups of the enzyme.

OBJECTIVES OF THE INVENTION

A major object of the present invention is to design a site-specific biomolecular complex for the selective transport of a therapeutic, prophylactic and diagnostic agent to the target brain cells. The lipophilic macromolecular carriers of a therapeutic agent are biocompatible with tissue components. The resultant lipophilic (agent:carrier) complexes, conjugates or transport vectors, containing highly unsaturated omega-3 moieties, assure selective uptake by similar lipid compositions of the cell membranes. The targeting complexes are further specific for agent delivery through receptor pathways in neuronal membranes or in astroglial cells.

Preferred features of the present invention are the design, synthesis and use of lipophilic targeting complexes to deliver the "required agent dose" in vivo, in controlled therapeutic levels of therapeutic or prophylactic agents in blood circulation or other body fluids, e.g., spinal fluid (SP).

SUMMARY OF THE INVENTION

The instant invention describes a site-specific therapeutic, prophylactic or diagnostic complex comprising a biologically active molecule and a residue of an omega-3 fatty acid. By complex or conjugate is meant a molecule that is either held together by van der Waal's and electrostatic interactions or by covalent bonds. The preferred omega-3 fatty acids are eicosapentaenoic acid, docosahexaenoic acid and linolenic acid. It should be noted that the specific bonding in the complex will be dictated by the specific chemistries used to form the complex of the invention.

The therapeutic complexes of the present invention are particularly useful for treating diseases that occur in the glial tissue of the brain as well as for treating diseases that occur in the cortical, cholinergic and adrenergic neurons.

The biologically active agent is selected from the group consisting of amino acids, peptides, poly peptides, proteins, fusion proteins, polyethylene glycol-derviatized proteins, enzymes, hormones, growth factors, antigens, antibodies, nucleic acids and derivatives thereof, DNA- and RNA-segments, oligonucleotides, antisense oligonucleotide analogs, nucleotides and derivatives thereof, genes, transfected cells, biological vectors, cloning vectors, expression vectors, neurotoxins and fragments thereof, and diagnostic agents.

The site-specific complex of the present invention may optionally further comprise a poly amino acid such as polylysine, polyarginine, polyornithine and polyasparagine. The preferred poly amino acid is a polylysine having 1–50 lysine residues and preferably from 10 to 25 lysine residues.

The site-specific complex of the present invention may optionally further incorporate a targeting moiety selected from the group consisting of the C fragment of tetanus toxin (TTC), alpha bungarotoxin (ABT) and nerve growth factor (NGF).

The instant invention is further directed to methods for the site directed delivery of drugs to treat diseases of the glial tissue of a mammalian brain by administering to the afflicted mammal a therapeutically effective amount of a biologically active agent, called also drug, that has been derivatized with eicosapentaenoic acid. When it is desired to treat diseases of the cortical, cholinergic and adrenergic neurons the agents are derivatized with docosahexaenoic acid.

It is further noted that if one desires to deliver a diagnostic agent to the above-mentioned parts of the brain, then the diagnosic agent is derivatized accordingly, i.e., eicosapentaenoic acid when glial delivery is required and docosahexaenoic acid when cortical, cholinergic and adrenergic neuron delivery is required.

The present invention further describes a transport vector comprising site-specific moiety covalently bonded to a poly-L-lysine carrier having a molecular weight of 1000 to 50,000 and further bonded (directly or indirectly) to one or more poly-unsaturated fatty acid residues. Alternatively, the site-specific moiety can be bonded to a phospholipid or diglyceride. The transport vector can be bound to 1 to 5 molecules of an active agent, such as an enzyme, by random coupling to pendant epsilon-amino groups of the carrier. Other coupling methods are also within the scope of the invention.

By controlling the molecular weight of the poly-L-lysine carrier, it is possible to regulate the penetration of the whole macromolecular vehicle (cationic at physiological pH) through the BBB in vivo, and to predict, design and fabricate the adequate drug delivery system with high performance in vivo.

The site-specific complex of the present invention which includes the active agent and cationic carrier will further contain one or more DHA or EPA moieties so the complexes may reach their sites of action more effectively. The number of DHA or EPA moieties in such complexes may vary from 1 to 20 moieties.

For example, in the site-specific complex, three different groups are attached to the main polymeric chain comprising a biodegradable homopolymer of poly-L-lysine.

One component of the complex is the active agent which is the entity that initiates the therapeutic or physiological response. It is attached to the carrier and is active only after being cleaved from the vehicle. The attachment of the agent can be to the main chain of the poly-L-lysine carrier or through an epsilon-amino group of the pendant chain (e.g., a side spacer) to the main polymer chain or even by covalent bonds to the hydrophobic part of the vehicle. Agent derivatization is preferred because the resulting peptide link between agent and carrier is stable in an aqueous media but readily hydrolyzed intracellularly by lysosomal enzymes. This last process can be optimized by using pH spacer molecules between agent and carrier. The agent can be an enzyme or a protein in a protected form with low enzyme antigenicity.

The site-specific moiety, which can be attached to poly-L-lysine or directly to the agent is a specific transport moiety for certain tissue cells. Examples of site-specific moieties are pH-sensitive groups or receptor-active components, such as antibody-antigen recognition, or protein fragments (e.g., tetanus toxin fragment C:TTC) compatible with a receptor on a specific cell surface, or neurotoxins, such as an antagonist, e.g., alpha-bungarotoxin:ABT for nicotinic acethylcholine receptor.

One or more hydrophobic groups can be attached to the macromolecular carrier by covalent bonds to enhance the lipophilic character of the polar agent vehicle. Increased lipophilicity aids incorporation of the complex into the lipid matrix of a cell.

The resultant site-specific complex can interact with water to form self-assembling structures in colloidal dispersions. Alternatively, the site-specific complex can be mixed with lipids, such as phosphatidyl choline and cholesterol, in aqueous systems to form liposomes by conventional methods. The pharmaceutical preparations can be administered in vivo where the said complex is attracted to the specific cell membrane and its uptake is enhanced. Therefore, the colloidal particles (e.g., micelles, vesicles or liposomes) are specifically targeting a cell surface determinant and subsequently internalized through endocytosis or pinocytosis.

The presence of a fusion protein (e.g., vital fusion proteins, influenza hemagglutinin) covalently coupled with the lipophilic moiety through the poly-lysine carrier or as a targeting moiety of the agent complex in delivery system enhances endocytosis of colloidal particles which are ultimately broken down in the lysosomes.

The fusion proteins (e.g., viral envelope glycoprotein of Sendai virus, influenza virus or herpes Simplex virus) have been exploited for cytoplasmic delivery of macromolecules which are membrane impermeable [Bentz J. et al, "Liposomes, membranes fusion, and cytoplasmic delivery", Chapter 20, in "The structure of biological membranes", Edited by Yeagle Ph., CRC Press, Boca Raton, 1992, pp. 915–947; Hoekstra, D. et al, "Cell biology of entry and exit of enveloped viruses", Chapter 21, in "The structure of biological membranes", Edited by Yeagle Ph., CRC Press, Boca Raton, 1992, pp. 949–996].

BRIEF DESCRIPTION OF THE DRAWINGS

FIG. 3 is a schematic representation of a site-specific biomolecular complex or a targeting vehicle for pharmacologic agents constructed by covalent linkage of a fatty acid or phospholipid molecule (represented by lipophilic moiety) to the agent (A) through a poly-L-lysine (PPL, wherein subscript N is between zero and 11), optionally coupled with another segment of poly-L-lysine (PPL, wherein subscript M is an integer having values between zero and 11) derivatized with a targeting moiety for selective drug delivery to the brain.

DESCRIPTION OF THE PREFERRED SPECIFIC EMBODIMENTS

Figure 1:
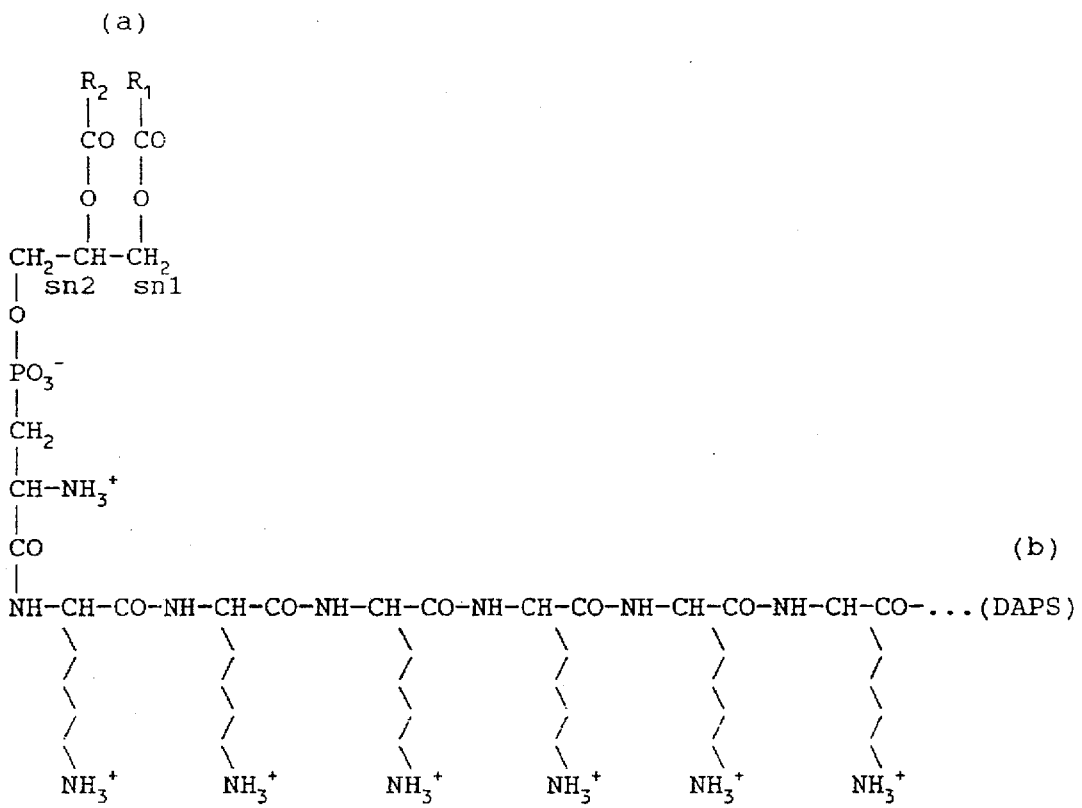
FIG. 1 shows a model of a lipophilic polylysine as an amphipathic conjugate or complex; (a): shows a lipophilic poly-L-lysine conjugate through a peptidic bond between alpha-amino terminal of the main polypeptide chain and free carboxylic group of diacyl phosphatidyl serine (DAPS). Also lyso-phosphatidyl serine may be used. (b): shows another derivative of poly-L-lysine and DAPS, covalently bound through a peptidic bond between the amino group of DAPS and the carboxyl therminal of the main polymeric chain (shown in the same FIG. 1 (b), by dotted line) or through a monoester bond of the main chain and diacyl glycerols. Also, phosphatidyl ethanol amine may be used. $R_1$ and $R_2$ represent alkyl chains of fatty acids of omega-3 or omega-6 series.

The lipophilic functional poly-unsaturated molecules which form part of the site-specific complex are preferably selected from the group consisting of fatty acids of the omega-3 series or lipid derivatives thereof. Other examples of lipophilic molecules are fatty acids, diacyl glycerols, diacyl phospholipids, lyso-phospholipids, cholesterol and other steroids, bearing poly-unsaturated hydrocarbon groups of 18 to 46 carbon atoms.

Preferred bio-polymer carriers are poly (alpha)-amino acids (e.g. PLL, poly L-arginine:PLA, poly L-ornithine:PLO), human serum albumin, aminodextran, casein, etc. These carriers are biodegradable, biocompatible and potentially excellent candidates for drug delivery systems.

The present invention is illustrated by the use of the following preferred specific embodiments, as non-limiting examples.

MACROMOLECULAR CARRIER

The macromolecular carrier is a polypeptide carrier exemplified by poly-L-lysine which is represented by the following structural formula:

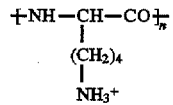

wherein subscript n denotes the number of L-lysine in the carrier.

Another variant of the poly-lysine carrier that is within this invention contains the lysines, either D- or L-configuration, linked alternatively by typical peptide bonds to each other.

Another polypeptide that is within the scope of this invention is a C-terminal and N-terminal arginine or the masked or blocked arginine. Preferred N-terminal amino acid groups are arginine, acetyl arginine, lysine or acyl lysine, where these terminal amino acids are of either D- or L-configuration. The amino acids that constitute the core sequence of the polypeptide of this invention are preferably in the L-isomer form. Characteristic features and structural/colloidal behavior of the polypeptides of this invention are essential to allow the proper polymer configuration/conformation to effect an increase of permeability of BBB when they are attached to a drug administered to the host animal. The host can be humans, domestic animals (e.g., dog, cat, horse, etc.), and animals for experimental purposes (e.g., rabbits, rats and mice) or any animal which possesses a central nervous system (i.e., a brain).

If the D-isomer of lysine is optionally added for one or more times in the linear core sequence of lysines, particularly in C-terminal region, the penetration of the drug-conjugates through the BBB might be altered, even diminished. In the preferred macromolecular embodiment of this invention the polylysine should be derived from the L-isomer.

Known preparative methods can be used for synthesis of PLL, with desired average molecular weight: MW. The hydrobromide salts of PLL of varying MW's are also commercially available, for example, hydrobromide salts of PLL of MW 3300–4000 (i.e., PLL with about 26 lysyls chain length) and of MW 180,000–260,000 (i.e., 1200–1700 lysyls in poly-lysine chain length), etc. In general, polypeptides with less than 20 amino acids are prepared by known solid phase synthesis.

Thus, a preferred embodiment of this invention is poly-L-lysine, noted also as PLL or poly-Lys, with n comprised between 6 and 25, sometimes at least 50 lysine molecules as a constituent part of a site-specific complex. For an understanding of the structural and functional role of poly-Lys as a macromolecular carrier we developed an artificial model system (i.e., a drug vehicle) using lipophilic poly-Lys carrier for drug delivery systems.

This invention also pertains to lipophilic poly-Lys conjugates or complexes wherein a wide variety of lipophilic compounds (e.g., highly unsaturated fatty acids or derivatives thereof) are covalently bound to linear (FIG. 1) or branched poly-Lys. Examples of highly unsaturated fatty acid derivatives such as phospholipids are, but not limited to those, listed in Table 1.

TABLE 1: PREFERRED SELECTED PHOSPHOLIPIDS TO BE USED AS LIPOPHILIC MOIETY 1. (rac)-1-O-octadecanoyl, 2-O-docosahexaenoyl-glycero-3-phospho-serine
2. (rac)-1-O-octadecyl, 2-O-docosahexaenoyl-glycero-3-phospho-serine
3. rac)-1-O-hexadecanoyl, 2-O-docosahexaenoyl-glycero-3-phospho-serine
4. (rac)-1-O-hexadecyl, 2-O-docosahexaenoyl-glycero-3-phospho-serine
5. (rac)-1-O-octadecanoyl, 2-O-eicosapentaenoyl-glycero-3-phospho-serine
6. (rac)-1-O-octadecyl, 2-O-eicosapentaenoyl-glycero-3-phospho-serine
7. (rac)-1-O-hexadecanoyl, 2-O-eicosapentaenoyl-glycero-3-phospho-serine
8. (rac)-1-O-hexadecyl, 2-O-eicosapentaenoyl-glycero-3-phospho-serine
9. (rac)-1,2-O-di-docosahexaenoyl-glycero-3-phospho-serine
10. (rac)-1, 2-O-di-docosahexaenoyl-glycero-3-phospho-ethanolamine
11. (rac)-1, 2-O-di-docosahexaenoyl-glycero-3-phospho-ethanol mono methyl amine
12. (rac)-1-O-hexadecyl, 2-O-docosahexaenoyl-glycero-3-phospho-carnitine
13. (rac)-1-O-docosahexaenyl, 2-O-docosahexaenoyl-glycero-3-phospho-carnitine
14. (rac)-1, 2-O-di-docosahexaenyl-glycero-3-phospho-carnitine
15. (rac)-1-O-hexadecyl, 2-O-docosahexaenoyl-3-[2-(2-mono methyl ammonio acetylamino)ethyl]phosphate
16. (rac)-1-O-octadecanoyl, 2-O-eicosapentaenoyl-glycero-3-phospho-ethanol amine acylated derivative
17. (rac)-1-O-eicosapentaenyl, 2-O-eicosapentaenoyl-glycero-3-phospho-serine
18. (rac)-1-O-eicosapentaenyl, 2-O-eicosapentaenoyl-glycero-3-phospho-ethanol amine acylated derivative.
19. (rac)-1, 2-O-di-eicosapentaenoyl-glycero-3-phospho-serine
20. (rac)-1, 2-O-di-dihomo-gamma-linolenoyl-glycero-3-phospho-serine
21. (rac)-1-O-dihomo-gamma-linolenoyl, 2O-docosahexaenoyl-glycero-3-phospho-serine
22. (rac)-1-O-dihomo-gamma-linolenoyl, 2-O-eicosapentaenoyl-glycero-3-phospho-serine The acyl derivatives of phosphatidyl serine (DAPS) are not critical, but in general (see, Table 1) will contain at least 16 carbon atoms. Preferably the fatty acyls $R_1$ and $R_2$ contain from 16 to 24 carbon atoms exclusive of additional side chains or functional groups. The fatty acyls may be saturated (in sn1-position of glycerol backbone) and poly-unsaturated of omega-3 or omega-6 essential fatty acid series (in sn2-position) or both poly-unsaturated with at least 18 carbon atoms. Suitable fatty acids include palmitic (PA), stearic (STA), linoleic (LO), linolenic (LA), arachidonic (AA), di-homo gamma linolenic (DGLA), eicosapentaenoic (EPA) and docosahexaenoic (DHA) acids.

Other lipophilic poly-lysine conjugates can be formed through one or more peptidic bonds between amino group(s) of the carrier and carboxylic group(s) of a poly-unsaturated fatty acid(s) of omega-3 or omega-6 series, preferably DHA, EPA and DGLA.

Another alternative to design lipophilic poly-Lys is by using branched poly-Lys, for example with a single lysine like a free block.

The lipophilic-PLL carrier of pharmaceutical compositions of this invention can also contain neuropharmaceutical agents which have a prophylactic and/or therapeutic effect on neurological disorders. For example, neurological disorders include: malignant brain tumors, autoimmune deficiency syndrome (AIDS), Parkinson's disease, neurodegenerative disease, Alzheimer's disease, multiple sclerosis, migraine, pain or a seizure disorder, epilepsy, depression and trauma, neuronal storage disease, and other severe deterioration of the CNS.

This invention also relates to the design of novel drug-vehicles or drug-shuttles with increased lipophilicity and increased penetration into biological membranes having facilitated transport throughout the body. The invention is also particularly useful for delivering to neuronal sites pharmaceutically active agents such as anti-neoplastic agents, anti-microbial agents, anti-parasitic agents, adrenergic agents and catecholaminergic agents, anti-convulsants, nucleotide analogues, anti-trauma agents, enzymes and proteins used to prevent or treat neurological disorders.

Figure 2:
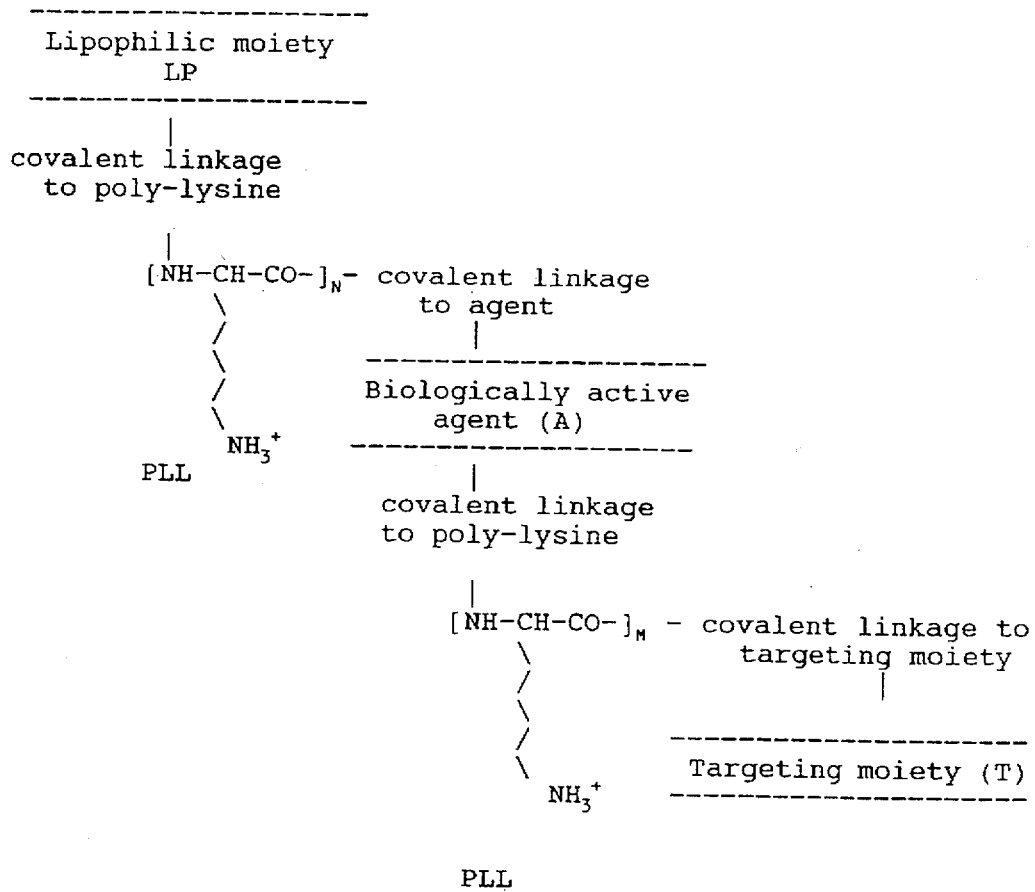
FIG. 2 is a schematic representation of a lipophilic site-specific biomolecular complex or a targeting vehicle for pharmacologic agents designed by covalent linkage of a fatty acid or a phospholipid molecule (noted as lipophilic moiety: LP) to the agent (A) through a poly-L-lysine (PLL, wherein subscript N has values between zero and 50, preferably 11 lysyls). Optionally, said complex is further coupled with another segment of poly-L-lysine (PLL, wherein subscript M comprises values between zero and 50, preferably 11 lysyls) derivatized with a targeting moiety (T) for selective agent delivery to the brain.
Figure 4:
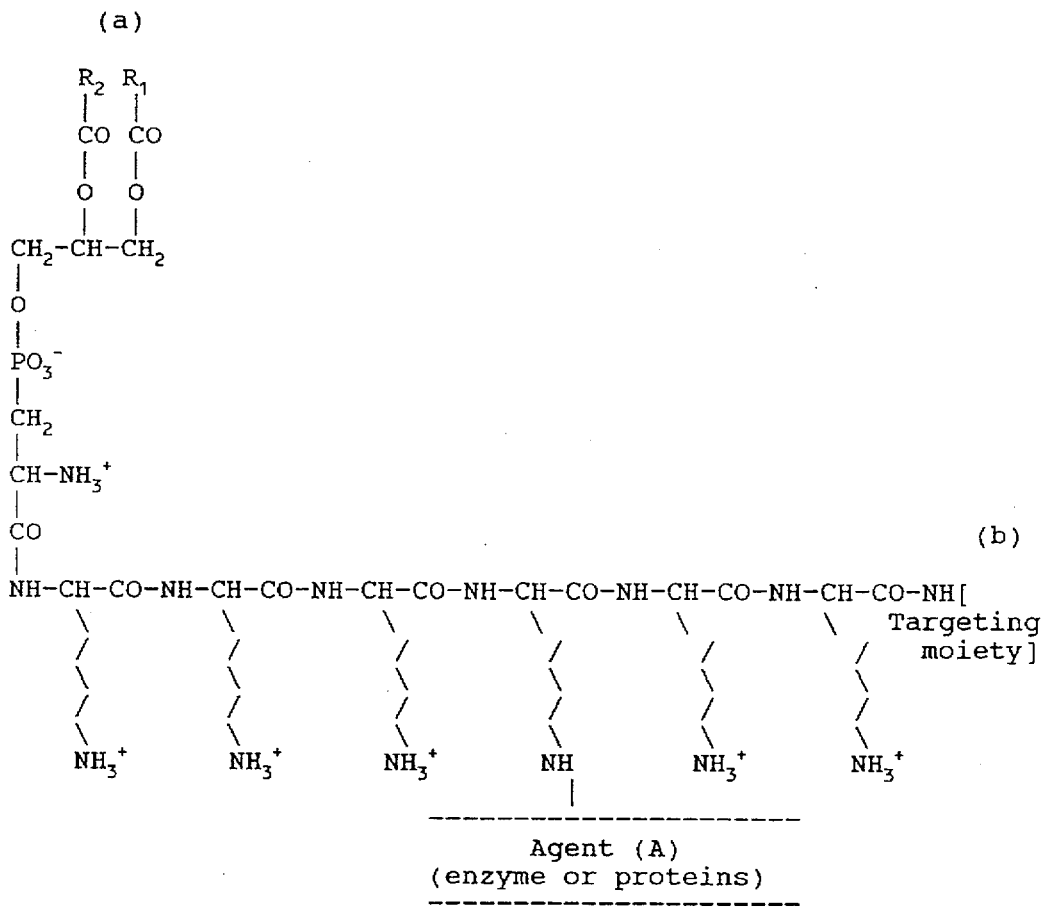
FIG. 4 is a schematic representation of a site-specific biomolecular complex or a targeting vehicle of an agent, wherein targeting moiety (b) is coupled with the terminal of the main polymeric chain, and the agent is coupled with epsilon-amino group of the side lysine chain, $R_1$ and $R_2$ the same or different, represent alkyl chains (a) saturated in sn1 position of glycerol moiety and poly-unsaturated in sn2 position, suitably of 18 to 46 carbon atoms with 3 to 6 or more double bonds, preferable docosahexaenoyl residue: $R_1$ and $R_2$: $CH_3$—$CH_2$—$(CH=CH-CH_2)_6$ —$CH_2$—. Phosphatidyl serine is coupled to main polymeric chain through its —COOH group.
Figure 5:
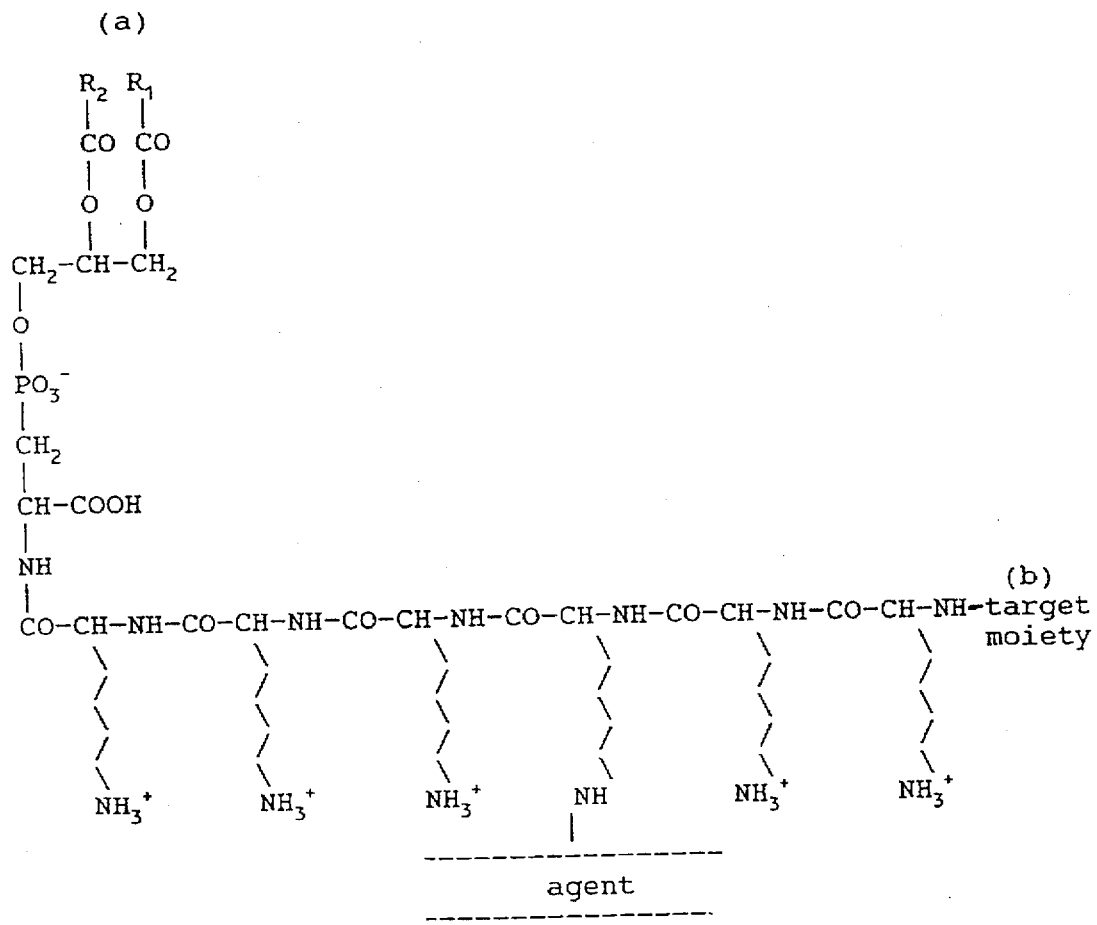
FIG. 5 is a schematic representation of a site-specific biomolecular complex or a targeting vehicle of the agent, wherein targeting moiety (b) is coupled with the terminal of the main polymeric chain, and the agent is coupled with epsilon-amino group of the side lysine chain, $R_1$ and $R_2$ the same or different, represent alkyl chains (a) saturated in sn1 position of glycerol moiety and poly-unsaturated in sn2 position, suitably of 18 to 46 carbon atoms with 3 to 6 or more double bonds, preferable docosahexaenoyl residue: $R_1$ and $R_2$: $CH_3$—$CH_2$—$(CH=CH-CH_2)_6$ —$CH_2$—. Phosphatidyl serine is coupled to main polymeric chain through its —$NH_2$ group.
Figure 6:
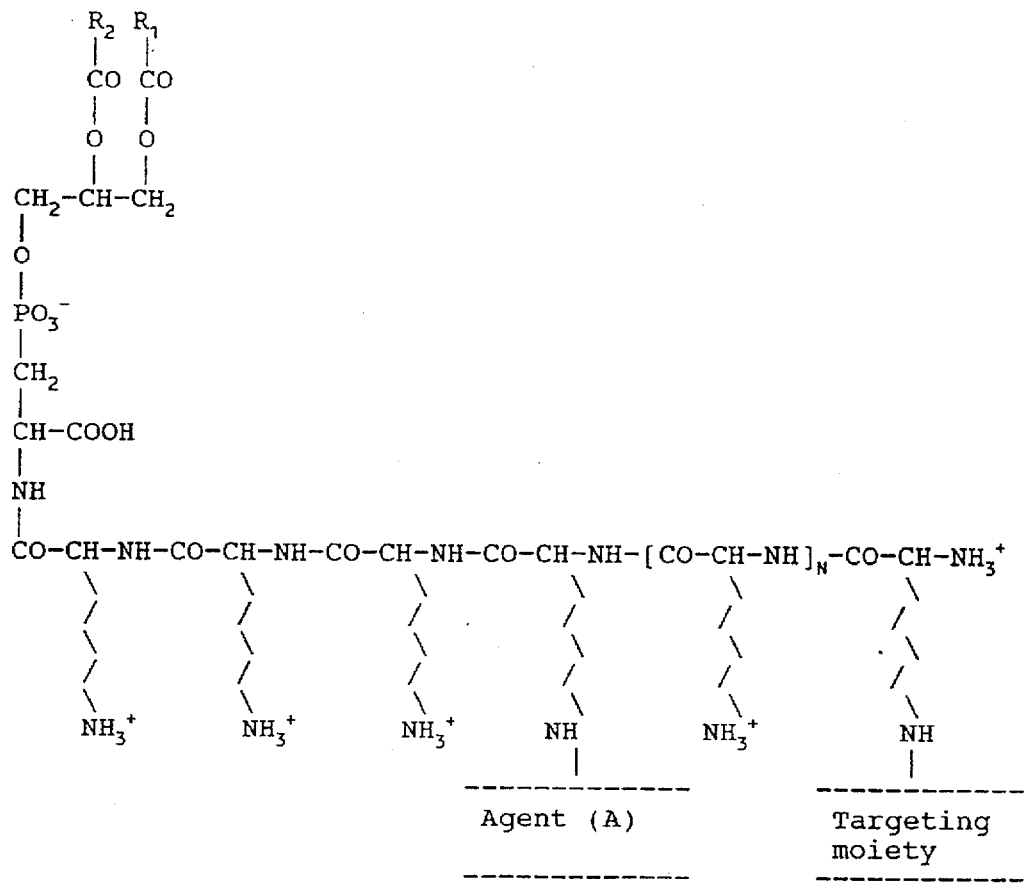
FIG. 6 is a schematic representation of a site-specific biomolecular complex or a targeting vehicle of the agent, wherein a targeting moiety and the agent are coupled with epsilon-amino group(s) of the side lysine chain, $R_1$ and $R_2$ the same or different, represent alkyl chains (a) saturated in sn1 position of glycerol moiety and poly-unsaturated in sn2 position, suitably of 18 to 46 carbon atoms with 3 to 6 or more double bonds, preferable docosahexaenoyl residue: $R_1$ and $R_2$: $CH_3$—$CH_2$—$(CH=CH-CH_2)_6$ —$CH_2$—. Phosphatidyl serine is coupled to main polymeric chain through its —$NH_2$ group. Subscript N has values between 1 and 25.
Figure 7:
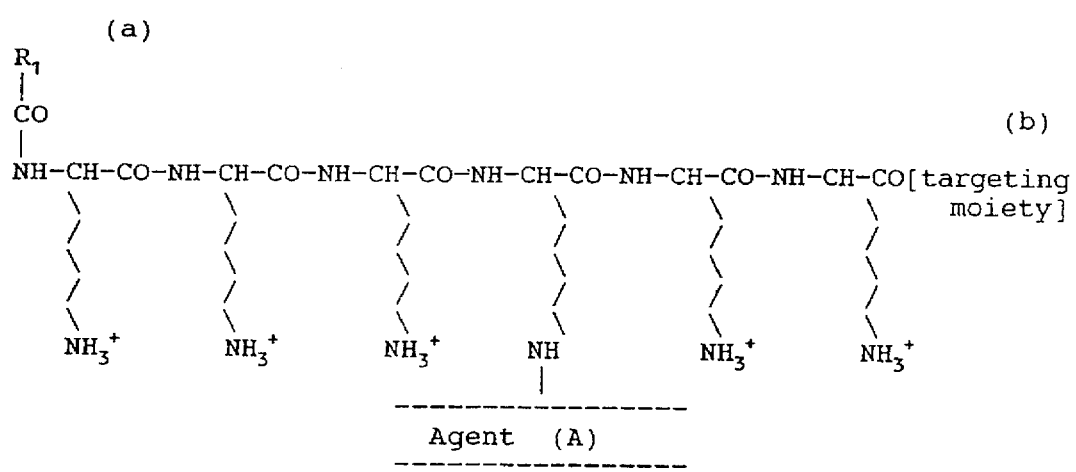
FIG. 7 shows a site-specific biomolecular complex or a targeting vehicle of a biologically active agent, wherein the agent is derivatized with a lipophilic carrier. Lipophilic moiety is represented by a fatty acid of omega-3 and omega-6 series (a), with hydrocarbon chain of 18 to 46 carbon atoms, preferable poly-unsaturated of 22 carbon atoms with 6 double bonds, i.e. docosahexaenoyl residue: $CH_3$—$CH_2$—$(CH=CH-CH_2)_6$—$(CH_2)$—. Targeting moiety is shown in the same figure (b).

In the model of targeting lipophilic complexes, (presented in FIG. 2), both the therapeutic agent and targeting moiety are attached at the terminals of the main linear chain of the poly-peptide. Alternative variants of the derivatization approach presented above (FIG. 2) in which the agent is coupled with epsilon-amino group of side lysyl chain (see FIGS. 3–7) or to branched poly-lysine are also preferred features of this invention.

From the description of novel concept of targeting lipophilic complexes or conjugates, and from the above examples, one skilled in the art can easily ascertain the characteristic essential features of this invention, without departing from invention objectives, and can make various changes in the invention complex model to adapt it to various usages and conditions.

The molecular conjugates of this invention are prepared conventionally by known methods in the art, as shown in the following examples.

PREPARATION OF ENZYMES COVALENTLY COUPLED WITH POLY-UNSATURATED FATTY ACIDS

General Description

The molecular conjugates of an agent (A), such as a biologically active enzyme (which can be noted E), with poly-unsaturated fatty acids, noted PUFA, may be represented by the general formula:

$$E-(PUFA)_{r=1,2,\ldots,20} \quad [1]$$

wherein r is an integer from 1 to 20, and PUFA is chosen from a group consisting of omega-3 essential PUFA, more preferably alpha-linolenic acid (ALA), eicosapentaenoic acid (EPA) and most preferably docosahexaenoic acid (DHA) and represented by the formula $R_1-COOH$.

These conjugates of formula [1] may be prepared by condensation of $R_1-COOH$ with the appropriate amine group(s) on the enzyme $E-NH_2$. Many methods for the formation of amides from acids and amines are known in the art. Among them, the use of carbodiimides is particularly recommended for compounds of the above general formula. The reaction for conjugation of E with PUFA is illustrated by:

$$E-NH_2 + HOOC-R_1 = E-NH-OC-R_1 + H_2O \quad [2]$$

The starting materials are readily available, or their synthesis and purification are well known in the art.

The enzyme derivatives of the present invention are particularly useful for treating lysosomal storage diseases which cause severe neurodegeneration and are manifested by enzyme deficiences. The specific enzymes which can be derivatized are, but not limited to those, listed in Table 2 [Neufeld, Annu. Rev. Biochem., 60:257–80 (1991)].

TABLE 2

| Lysosomal Storage Diseases | |
|---|---|
| Disorder | Deficient Enzyme |
| 1. Sphingolipid degradation | |
| Farber's disease | ceramidase |
| Fabry's disease | alpha-galactosidase |
| Gaucher's disease | glucocerebrosidase |
| $G_{M1}$ gangliosidosis | beta-galactosidase |

TABLE 2-continued

| Lysosomal Storage Diseases | |
|---|---|
| Disorder | Deficient Enzyme |
| $G_{M2}$ gangliosidosis: | |
| Tay-Sachs disease | beta-hexosaminidase A |
| Sandhoff disease | beta-hexosaminidase A & B |
| Activator deficiency | $G_{M2}$ activator |
| Krabbe disease | galactosylceramidase |
| Metachromatic leukodystrophy | |
| enzyme-deficient form | arylsulfatase A |
| activator-deficient form | sulfatide activator/saposin |
| Mucolipidosis IV | ganglioside sialidase |
| Multiple sulfatase deficiency | all sulfatases |
| Niemann-Pick disease | sphingomyelinase |
| Schindler disease | alpha-N-actylgalactosaminidase |
| 2. Glycoprotein degradation | |
| Aspartylglycosaminuria | aspartylglycosaminidase |
| Fucosidosis | alpha-L-fucosidase |
| Galactosialidosis | protective protein/cathepsin, beta-galactosidase and sialidase |
| alpha-Mannosidosis | alpha-mannosidase |
| beta-Mannosidosis | beta-mannosidase |
| Sialidosis | sialidase |
| 3. Glycosaminoglycan degradation | |
| Hunter syndrome | iduronate sulfatase |
| Hurler and Scheie syndromes | alpha-L-iduronidase |
| Maroteaux-Lamy syndrome | GalNAc 4-sulfatase/arylsulfatase B |
| Morquio syndrome | |
| A subtype | Gal 6-sulfatase |
| B subtype | beta-galactosidase |
| Sanfilippo syndrome | |
| A-subtype | heparan N-sulfatase |
| B-subtype | alpha-N-acetylglucosaminidase |
| C-subtype | AcetylCoA: glucosamine N-acetyltransferase |
| D-subtype | GlcNAc-6-sulfatase |
| Sly sndrome | beta-glucuronidase |
| 4. Other single enzyme deficiency disorders | |
| Pompe disease (glycogenois II) | alpha-glucosidase |
| Wolman disease | acid lipase |
| 5. Disorders of lysosomal enzyme biosynthesis | |
| I-cell disease and pseudoHurler polydystrophy | 6-phosopho-N-acetylglucosamine transferase |
| 6. Disorders of lysosomal membrane transport | |
| Cystinosis | cystine transport |
| Sialic storage and Salla disease | sialic acid transport |

The coupling of PUFA with reactive amino acids on enzyme, preferably lysine through its epsilon amino group or with the N-terminal amino group of the enzyme, may be achieved through amide bond as shown in reaction [2].

The reaction product, $$E-(NH-OC-R_1)_{r=1,2,\ldots,20} \quad [3]$$

wherein r is an integer from 1 to 20 which shows the varying numbers of lipophilic residues attached to the enzyme macromolecule and is controlled primarily by the ratio of PUFA to lysyls of enzyme chain length and secondarily by the duration of the coupling reaction. The composition and structure may be determined for any condensation product by the known method in the art (Lowry et al., J. Biol. Chem., 193, 265–275 (1951)).

The conditions for reaction [2] are conventional conditions for the formation of an amide linkage, such as by activating the fatty acid (HOOC—$R_1$) with a suitable activator under non-aqueous conditions, for example dicyclohexylcarbodiimide, and subsequent reaction with the appropriate amine group(s) on enzyme. During reaction, pH may be controlled, if necessary, by acid or base addition either manually or automatically.

After the conjugation reaction is complete, excess reagent and unwanted reaction products may be removed by suitable techniques known in the art, including chromatographic procedures, for example gel filtration, dialysis and diafiltration, etc. Such conjugations are further described by examples 1 to 3.

EXAMPLE 1

In a practical example, an enzyme is dissolved in an aqueous buffer preferably at a moderately alkaline pH 7–9.5 (e.g. phosphate buffered saline: PBS). At a temperature in the range of 0° to 40° C., the solution of enzyme is treated with 0.6 equivalents of PUFA dissolved in non-aqueous medium in the presence of 1 equivalent of suitable carbodiimide, preferably dicyclohexylcarbodiimide, under the argon and suitable anti-oxidant compounds to protect from damage the PUFA during the conjugation reaction. The reaction is permitted to proceed for about 17 hours at ambient temperature. Then the reaction mixture is passed through Sephadex columns. The reaction product provides around 2 PUFA residues per enzyme, (see formula [3]).

In a similar manner, various molecular conjugates with different stoichiometric ratios of PUFA per enzyme molecule could be prepared.

Carbodiimide coupling is a well-known procedure outlined in the following literature references: Sheehan, J. C. and Hess, G. P., "New method of forming peptide bonds", J. Am. Chem. Soc., 77, 1067 (1955); Halloran, M. J. and Parker, C. W., "The preparation of nucleotide-protein conjugates: Carbodiimides as coupling agents", J. Immunology, 96, 373 (1966); Kurzer, F., and DouraghiZadeh, K., "Advances in the chemistry of carbodiimide", Chem. Rev., 67, 107 (1967); Carraway, K. L. and Koshland, Jr., D. E., "Modification of proteins by carbodiimide reaction", Methods in Enzymology, Vol. 25B, p. 616 (1972).

The molecular conjugates of enzyme and PUFA within this invention are also prepared conventionally as illustrated in examples 2 and 3.

EXAMPLE 2

Method for preparation of enzyme covalently coupled with PUFA using the conjugation reaction between enzyme and N-hydroxysuccinimide ester of PUFA in phosphate buffered saline (PBS) at pH 6–9.5, containing deoxycholate. For example, 3 mg of purified enzyme is added to 50 microgramms of N-hydroxysuccinimide ester of docosahexaenoic acid in PBS containing 2–3% deoxycholate. The mixture is incubated at 37° C. for 9 to 15 hrs and then chromatographed on a Sephadex G-75 column (1.3×45 cm) in PBS containing 0.15% deoxycholate to remove excess of PUFA. Such reactions are described in the prior art: Huang et al., J. Biol. Chem., 255(17), 8015–8018 (1980), Lapidot et al., J. Lipid Res., 8, 142–145 (1967).

EXAMPLE 3

Conjugation of the enzyme with fatty acids of omega-3 series (such as, DHA) can be carrier out according to known procedures for reacting amino groups on enzyme with carboxyl group of poly-unsaturated fatty acids (as shown in example 1) or with their acyl chlorides or anhydrides. For example, enzyme is dissolved in bicarbonate buffer (BB, of pH 9); then PUFA-anhydride, dissolved in anhydrous dimethyl sulfoxide (DMSO), is added immediately to the enzyme solution. Enzyme-PUFA complexes of formula [1] are prepared. The stoichiometric ratio of PUFA/Enzyme could be varied as justified already. The reaction is allowed to proceed for 2 hours at 25° C. Then, the reactants were passed through G-25 Sephadex columns (using the procedure of U.S. Pat. No. 5,230,883). In a similar manner, PUFA-polymer conjugates at desired stoichiometric ratio, i.e. at a particular value of r in formula [1] can be prepared by routine experiments as stated above.

Various changes and permutations of the constituents of the transport vector of an enzyme, (e.g., of the lipophilic enzyme conjugates), can be further derivatived through several examples:

The reaction product,

  [4]

of an enzyme derivatized with PUFA and chemically linked to a protective moiety to decrease the enzyme antigenicity, e.g. human serum albumin (SA) or polyethylene glycol (PEG), is a non-immunogenic, protected-enzyme-PUFA conjugate.

The reaction product,

  [5]

is a targeted non-immunogenic, protected enzyme-PUFA vehicle, wherein T stands for the targeting moiety for specific delivery of the resultant conjugates to selective cellular surface receptors. T is selected from the group consisting of tetanus toxin fragment C (TTC), nerve growth factor (NGF), alpha-bungarotoxin (ABT), cell-surface directed antibodies (such as immunoglobulin G, antibody against human pancreatic tumor cells, and antibody against hepatocytes) and insulin as an example of a serum hormone used as targeting moiety, depending on the desired site of delivery.

The reaction product, $$T—S—SA—S—E—(PUFA)_{r=1,2,\ldots,20} \quad [6]$$

is an acid sensitive targeting non-immunogenic, protected enzyme-PUFA conjugate, i.e., a large, complex vehicle targeting non-immunogenic and protected enzyme-PUFA conjugate, designed for a cytoplasmic delivery of the enzyme after parenteral administration (in blood circulation). S is a spacer molecule which is pH sensitive. Accordingly, the resultant molecular conjugate [6] is designed for specific cytoplasmic delivery of the enzyme.

Various reaction products involved in the synthesis of the resultant enzyme conjugates of [6] are achieved using sequential step reaction procedures (see, conjugates of [4] and [5]).

PREPARATION OF ENZYMES (OR PROTEINS) COVALENTLY COUPLED WITH POLY-UNSATURATED FATTY ACIDS AND TARGETING MOIETIES AND/OR CARRIERS

Some of the various reaction products involved in the synthesis of molecular conjugates using step reaction procedures are shown below.

As targeting moieties: T, tetanus toxin fragment C :TTC or poly L-lysine:PLL are used as examples, but not limited to them. PLL could be used as a targeting moiety in terms of effecting cellular uptake of its molecular conjugates to an agent (enzyme) and also as a cationic transport carrier under the physiological conditions.

The molecular conjugates of a biologically active enzyme (or a therapeutic agent:A), which is noted as E, with poly-unsaturated fatty acids, noted as PUFA and symbolised by $R_1$—COOH, E are also covalently coupled with targeting moieties T, and may be represented by the following formula:

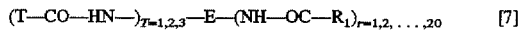
[7]

wherein subscript T is an integer with varying values from 1 to 3 and r has the known meaning. Briefly, the molecular conjugates of [7], can be written as T—E—PUFA conjugates, where covalent linkages between different parts of the transport vehicle are omitted, for the sake of simplicity.

The resulting T—E—PUFA conjugates [7] are synthesized by carbodiimide coupling procedure. Also, the T—E—PUFA conjugates can be achieved by a complex method, using glutaraldehyde coupling procedure and carbodiimide coupling procedure, and the resulting conjugates are given by [8]:

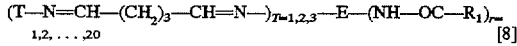
[8]

Permutations of the constituents on the transport vector [7] give new E—T—PUFA conjugates of [9]:

[9]

The E—T—PUFA conjugates are synthesised by carbodiimide coupling procedure. Also, the E—T—PUFA conjugates [10]:

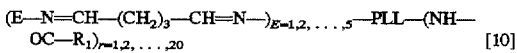
[10]

are prepared in two steps using both glutaraldehyde coupling procedure and carbodiimide coupling procedure.

Similar various molecular conjugates of an enzyme, chemically coupled with PLL carrier and with PUFA are given by [11]:

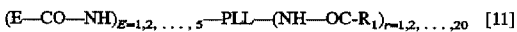
[11]

wherein subscript E is an integer with values from 1 to 5 and shows the plurality of the agent (noted A or E, when is particularised by an enzyme) on the transport vectors. The E—PLL—PUFA conjugates represented by [11] are achieved by carbodiimide coupling procedure. Also, similar E-PLL-PUFA conjugates given by [12]:

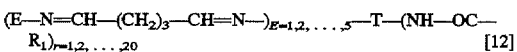
[12]

are prepared in two steps using glutaraldehyde coupling procedure and carbodiimide coupling procedure.

Molecular conjugates of an agent (i.e., enzyme) with PLL carriers, targeting moiety and PUFA are given by [13]:

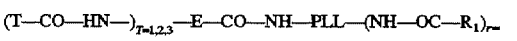
[13]

The resulting T—E—PLL—PUFA molecular conjugates are prepared in three steps using carbodiimide coupling. Also, a mixed method using a combination of glutaraldehyde coupling procedure and carbodiimide coupling procedure could be achieved and the resulting T—E—PLL—PUFA molecular conjugates are illustrated by [14]:

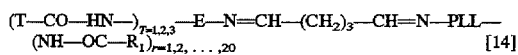
[14]

Various changes and permutations of the constituents on the transport vectors [14] can be realized and the resulting conjugates are illustrated by [15]:

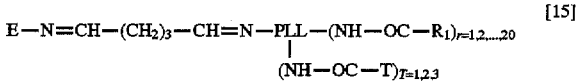
[15]

The resulting conjugates of [15] could be symbolized by E—PLL (T)—PUFA.

Further, a pH-sensitive spacer molecule (noted as S) can be inserted between agent (such an enzyme) and PLL carrier or between other parts of the transport vehicles, depending on the desired properties of the resulting final conjugate. Examples are illustrated by [16] and [17]:

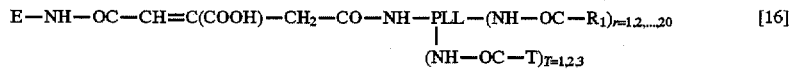
[16]

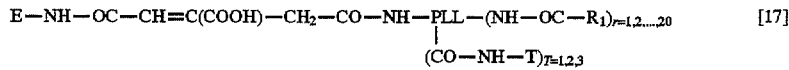
[17]

The resulting conjugates given by [16] and [17] can be symbolized by E—S—PLL (T)—PUFA.

Accordingly, conjugation can be achieved by chemical reactions, using step reaction procedures, well known in the art, employing carbodiimide catalyst, or combinations of glutaraldehyde coupling and carbodiimide coupling modes.

EXAMPLES OF STEP REACTION PROCEDURES

The molecular conjugates [7] of the following formula (T—CO—HN—)$_T$—E—(NH—OC—$R_1$)$_r$, written also in T—E—PUFA form, wherein subscripts T and r have their known meaning, are prepared conventionally in two steps.

In step I, there is described and obtained a conjugated product of enzyme with PUFA, i.e., E—(NH—OC—$R_1$ )$_r$, as shown in examples 1 to 3.

In step II, the conjugated product of step I, E—(NH—OC—$R_1$ )$_r$, is covalently coupled with a specific target moiety. This reaction is carrier out according to known procedures for reacting amino groups on enzyme with carboxyl groups of the targeting moiety to provide linkage between them, for example using carbodiimide coupling as in step I (see, example 1).

Other modes of conjugation can be used, depending on the structure and properties of the individual molecules employed to build the vehicle. For example, conjugation can be made by using bifunctional protein modifying reagents, such as glutaraldehyde, resulting in the following conjugated product of [8], (T—N=CH—(CH$_2$)$_3$—CH=N—)$_T$—E—(NH—OC—$R_1$)$_r$, represented further by formula T—E—PUFA.

The conjugated T—E—PUFA product can also be achieved by the following reactions:

T—NH$_2$+H$_2$N—E+H—CO—(CH$_2$)$_3$—CO—H→T—N=CH—
(CH$_2$)$_3$—CH=N—E          [18]

T—N=CH—(CH$_2$)$_3$—CH=N—E—NH$_2$+HOOC—R$_1$→(T—
N=CH—(CH$_2$)$_3$—CH=N—)$_T$—E—(NH—OC—R$_1$)$_r$,   [19]

The conjugation reaction [18] may be achieved using a variety of bifunctional protein modifying reagents. Examples of such reagents include: N-succinimidyl-3-(2-pyridyldithio)propionate, active esters such as disuccinimidyl suberate, aldehydes such as glutaraldehyde used in reaction [18].

Glutaraldehyde coupling is described in the prior art: Avrameas, S. and Ternynek, T., "Peroxidase labelled antibody and Fab conjugates with enhanced intracellular penetration", Immunochemistry, 8, 1175–1179 (1971); Gonatas, N. K., Kim, S. U., Stieber, A. and Avrameas, S., "Horseradish peroxidase-lectin conjugates", J. Cell Biol., 73, 1–13 (1977). Undoubtedless, other modes of conjugation can be used, depending on the structure and properties of the individual molecules employed to build the vehicle.

The conjugated product of reaction [18] is further derivatized with PUFA, following the procedure of reaction [19].

In a similar manner, a wide variety of molecular conjugates with different stoichiometric ratios of PUFA per enzyme molecule could be prepared.

Alternatively, conjugates of formulae [9] to [17] can be made in the intermediate steps, depending on the enzyme placement in the conjugated individual vehicle molecule.

As targeting moiety, tetanus toxin fragment C :TTC can be used as an example, but not limited to.

EXAMPLE 4

Preparation of Lipophilic Poly-lysine by Conjugation of Poly-lysine to Poly-unsaturated Fatty Acids The reactants of example 1 are used, except that 10 mg of the hydrobromide salts of poly-L-lysine: PLL of average molecular weight of 3300–4000 (containing about 25 lysyls in PLL chain length) is substituted for the enzyme. The quantity of PUFA, such as DHA, is calculated for a chosen stoichiometric ratio PUFA/PLL of two. The molecular complex of (DHA)$_2$—PLL is purified as known in the art.

EXAMPLE 5

Preparation of Molecular Conjugates of Poly-lysine with Phospholipids as Phosphatidyl Serine The reactants of example 4 are used, except that phosphatidyl serine ( (rac)-1-O-octadecanoyl, 2-O-docosahexaenoyl-glycero-3-phospho-serine, named also -1-O-stearoyl, 2-O-docosahexaenoyl-glycero-3-phospho-serine:SDPS) is substituted for the PUFA with the stoichiometric ratios of 2 for SDPS/PLL-macromolecule.

EXAMPLE 6

Molecular Conjugates of Poly-lysine with Phospholipids

In a similar manner, as in example 5, but using a large variety of other phospholipids (sn1-saturated, sn2-poly-unsaturated, or both chains poly-unsaturated) similar derivatives can be prepared.

EXAMPLE 7

Conjugation of Enzyme to Molecular Conjugates of Poly-lysine with Poly-unsaturated Fatty Acids (Docosahexaneoic Acid: DHA)

The reactants of example 1 are used, except that molecular conjugate of poly-lysine with DHA (product of example 4) is used to substitute for the PUFA. The quantity of said reactants, is calculated for a chosen stoichiometric ratio (see formula [9]) within the desired limits for the hydrophilic hydophobic balance of the resultant transport vector of enzyme. The final molecular complex of lipophilic enzyme must be present with at least 70% of cationic charges initially available (unmodified PLL) for excellent uptake into cell.

EXAMPLE 8

Synthesis of PLL-(SDPS)$_2$ (Poly Lysine and Diacyl Phosphatidyl Serine) Conjugates PLL-(SDPS)$_2$ conjugates or complexes are synthesized by coupling SDPS to the alpha-amino group and to the carboxyl group of a suitably protected epsilon-amino PLL molecule (e.g., about 12 lysyls in a PLL chain length) using carbodiimide coupling procedure in a similar manner as in example 4.

The reactants of example 4 are used, except that sodium salt of phosphatidyl serine ( (rac)-1-O-octadecanoyl, 2-O-docosahexaenoyl-glycero-3-phospho-serine, named also -1-O-stearoyl, 2-O-docosahexaenoyl-glycero-3-phospho-serine:SDPS) is substituted for the PUFA with the stoichiometric ratios of 2 for SDPS/PLL-macromolecule and PLL molecule has epsilon-amino groups protected.

Briefly, the coupling reaction entailed adding a 2% solution of SDPS in ethanol in aliquots to a stirred 0.1% solution of the modified (epsilon-amino protected) PLL in 0.01 mol/l carbonate buffer at pH 9, or 0.01 mol/l phosphate buffer at pH 7.5 in the carbodiimide presence, at 0° C. The input molar ratio of SDPS to PLL is two (i.e., 1 SDPS to 6 lysyls), and of buffer to ethanol, 100:1 (v/v). Stirring was continued for 3 hours and the reaction was allowed to proceed overnight (about 14 hrs) at 4° C. under the argon and in the presence of antioxidants to protect poly-unsaturated compounds against oxidation. The resulting solution was dialyzed extensively against water or 0.1 mol/l NaCl (pH 7.3) for 3 days. Protecting groups were removed completely from PLL molecular conjugate with HBr in glacial acetic acid. The deprotection was confirmed by ultraviolet spectroscopy at 254 nm.

The SDPS content of the conjugates is determined spectrophotometrically and the analytical data on conjugates show that SDPS is coupled to alpha-amino group and to carboxylic terminal group of PLL molecule.

EXAMPLE 9

Covalent Bonding of Enzymes to PUFA'S and to Targeting Moieties

The molecular conjugates of the type [7]:

(T—CO—HN—)$_{T=1,2,3}$—E—(NH—OC—R$_1$)$_{r=1,2,...,20}$   [7]

are prepared conventionally in two steps. The molecular conjugate of the first step, enzyme derivatized with PUFA, such as DHA, described in examples 1–3 is covalently coupled, in a second step of conjugation reaction, to a specific targeting moiety, such as tetanus toxin fragment C (TTC). The second conjugation is carrier out according to known procedures, for example, reacting amino groups on enzyme with carboxyl groups of targeting moiety (if available) to provide linkage between them.

EXAMPLE 10

Preparation of Enzyme-polylysine-PUFA Conjugates

The molecular conjugates of the type [11]:

(E—CO—NH)$_E$—PLL—(NH—OC—R$_1$)$_r$,   [11]

wherein E is an integer with values from 1 to 5 and PLL is a cationic polymeric-carrier, such as poly-lysine with different molecular weigths, are prepared conventionally in two steps. For the sake of simplicity, the value of E=r=1 is chosen.

The molecular conjugate of the first step, PLL derivatized with PUFA, such as DHA, described in example 4, is covalently coupled, in a second step of conjugation reaction, to a specific enzyme. The second conjugation is carrier out according to known procedures, for example, reacting amino groups on PLL with carboxyl groups of enzyme (if available) to provide linkage between them.

Briefly, crystalline enzyme (glucocerebrosidase), poly-L-lysine (of molecular weight of 6700) derivatized with DHA at alpha-amino group, and 1-ethyl-3-(3-dimethyl-aminopropyl)carbodiimide (EDC) were dissolved in equal amounts of 10 mg each in 1 ml water. This solution was incubated at room temperature (around 22° C.) for 7 hours under argon with occasional shaking, and then loaded onto a Sephadex G-100 chromatographic column which had been previously equilibrated with 0.01M phosphate buffered saline (PBS), pH 7. After loading, the column was eluted with PBS and fractions containing enzyme coming out of the column at and around the void volume were collected, pooled, concentrated to a volume of 1.0 ml, and then diluted with water to a volume of 10 ml. In order to remove unreacted enzyme, this solution was passed through a DEAE-Sephadex column.

EXAMPLE 11

Conjugation of Horseradish Peroxidase to PLL-DHA Conjugates

The coupling modes and reactants of previous example 10 were used except that 10 mg of horseradish peroxidase (HRP) was taken for enzyme.

The HRP—PLL—DHA conjugates were used in experiments. The enzymatic activity of the pooled HRP—PLL—DHA conjugates was compared to that of unconjugated HRP using an assay employing dianizidine as an electron acceptor (see, U.S. Pat. No. 4,847,240). It was found that the conjugation decreased the enzymatic activity of HRP by about 40%.

Each elution fraction was also tested for transport into L929 fibroblast cells. The results show that the HRP—PLL—DHA fractions (conjugates) which enter cells most effectively are the first fractions eluted from the Sephadex column, hence the fractions containing the conjugates of largest molecular weight.

EXAMPLE 12

Acidity Sensitive Molecular Conjugates of Enzyme-spacer-PLL-PUFA Optionally Coupled with Targeting Moieties Molecular conjugates of the general form [16]:

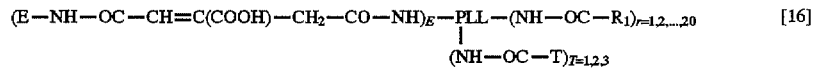

are prepared by linking the enzyme to the PLL carrier through an intermediate molecule, such as maleic anhydride, or copoly (ethylene maleic anhydride), or more preferable cis-aconitic acid, known as pH-sensitive spacer molecules, illustrated for E=T=r=1.

Therefore, a preferred molecular conjugate can be given either by formulae [20] or [21]:

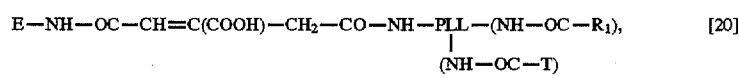

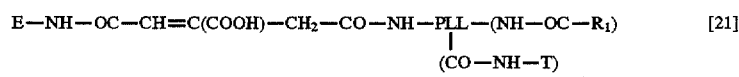

Other modes of carrying out this invention can be proposed using spacer molecules which contain more than one maleic anhydride ring, i.e., poly maleic anhydride, also commercially available.

The molecular conjugate of example 12 presents the advantage that is pH sensitive and in mild acidic conditions will release easily the enzyme in unmodified form, which is in a biologically active state. Using these molecular conjugate of example 12 it is possible to control the intracellular release of the enzyme (e.g., within the lysosome).

Using poly-anhydride, each pair of cis-carboxyl groups formed by hydrolyzing a maleic anhydride is believed to comprise a suitable location for bonding an enzyme molecule. Therefore, numerous enzyme molecules may be bonded to a single polymeric spacer molecule, as shown in formula [22]:

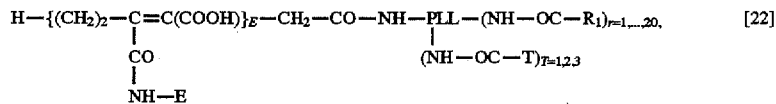

Molecular conjugates of formulae [22] show high efficiency to transport and release numerous enzyme molecules using a single transport vector. The use of a polymeric spacer molecule with poly cis di-carboxylic groups, such as in formula [22], allows for an efficient transport of enzyme (or proteins) in cell lysosomes, and assures a spontaneous release of all enzyme molecules when the resultant conjugate is subjected to acidic conditions.

Various preferred embodiments (e.g., formulae [16], [20]–[22]) within the instant invention can also be achieved by altering the sequence of reactions.

Examples 1 to 12 can be extended by using a wide variety of phospholipids, such as phosphatidyl ethanol amine, acylated phospholipids, lysophospholipids and or diacyl glycero derivatives and phosphatidic acids with the proviso that PUFA chains are in sn2 position or in both sn1 and sn2 position, if they are available.

The amount of different constituents of the vectored transport vehicle (e.g., agent, such as enzyme, proteins, factors, cofactors, hormons, anti-cancer drugs, anti-Parkinson's drugs, etc., carrier, such as PLL of varying moleculart weights, different lipophilic residues, and optionally targeting moieties) and all conditions of coupling reactions could be varied so long as the final resultant lipophilic conjugates have a lipophilic-hydrophilic balance within the desired range to assure the transport of the agent intracellularly and controlled release in cell lysosome.

From the proceeding description of novel concept of targeting/vectored lipophilic vehicles, conjugates or complexes, and from the above examples, one skilled in the art can easily ascertain the characteristic essential features of this invention, without departing from the invention objectives, and can make various changes in the invention of site-specific biomolecular complex, conjugate or vehicle model to adapt it to various usages and conditions.

Also, those skilled in the art will recognize many equivalents to the specific embodiments of the invention described herein. For example, it is believed that noncovalent bondings could be employed within this invention if the bond strength approached that of the covalent bonds. Accordingly, those equivalents are considered to be part of this invention and are intended to be emcompassed by the scope of the following claims.

References Cited

U.S. Patent Documents

| | | | |
|---|---|---|---|
| 5,308,701 | 5/1994 | Cohen, et al. | 428/402.22 |
| 5,296,483 | 3/1994 | Bodor | 514/217 |
| 5,225,182 | 7/1993 | Sharma | 424/9 |
| 5,268,164 | 12/1993 | Kozarich, et al. | 424/9 |
| 5,222,982 | 6/1993 | Ommaya | 623/12 |
| 5,187,158 | 2/1993 | Bodor | 514/13 |
| 5,144,011 | 9/1992 | Shen et al. | 530/391.5 |
| 4,935,465 | 6/1990 | Garman | 525/54.1 |
| 4,847,240 | 7/1989 | Ryser et al. | 514/12 |
| 4,701,521 | 10/1987 | Ryser et al. | 530/322 |
| 4,631,190 | 12/1986 | Shen et al. | 424/85.5 |
| 4,046,722 | 9/1977 | Rowland | 530/362 |

Other Publications:

1). Park, K., Shalaby, W. S. W., and Park, H., "Biodegradable hydrogels for drug delivery", Technomic Publ. Comp., Inc., 1993.

2). Audus, K. L., and Raub, T. J., "Lysosomes of brain and other vascular endothelia", in "The blood-brain barrier: Cellular and molecular biology", Edited by Pardridge, W. M., Raven Press, Ltd., New York, 1993, pp. 201–227.

3). Bentz J., Alford, D., and Ellens, H., "Liposomes, membrane fusion, and cytoplasmic delivery", Chapter 20, in "The structure of biological membranes", Edited by Yeagle Ph., CRC Press, Boca Raton, 1992, pp. 915–947.

4). Hoekstra, D. and Nir, S., "Cell biology of entry and exit of enveloped viruses", Chapter 21, in "The structure of biological membranes", Edited by Yeagle Ph., CRC Press, Boca Raton, 1992, pp. 949–996.

5). Ottenbrite, R. M., "Biologically Active Polymers", Chapter 1, in "Polymeric Drugs and Drug Delivery Systems", Edited by Dunn, R. L., and Ottenbrite, R. M., American Chemical Society, Washington, D.C., 1991, pp. 3–10.

6). Maruyama, K., Mori, A., Kennel, S. J., Waalkes, M. V. B., Scherphof, G. L., and Huang, L., "Drug Delivery by Organ-Specific Immunoliposomes", Chapter 24 in "Polymeric Drugs and Drug Delivery Systems", Edited by Dunn, R. L., and Ottenbrite, R. M., American Chemical Society, Washington, D. C., 1991, pp. 275–284.

7). Lundberg, B., "Techniques for Complexing Pharmacological Agents to Lipoproteins and Lipid Microemulsions", Chapter 3, in "Lipoproteins as carriers of pharmacological Agents", Edited by Shaw, J. M., Marcel Dekker, Inc., New York, 1991, pp. 97–139.

8). Leserman, L. D., "Immunologic targetting of liposomes", in "Liposomes, drugs and immunocompetent cell functions", Edited by Nicolau, C., and Paraf, A., Acad. Press, New York, 1981, pp. 109–122.

9). Ryser, H. J.-P., "Uptake of protein by mammalian cells: An underdeveloped area", Science, 159, 390–96 (1968), and Ryser, H. J. -P., "Poly(amino acids) as enhancers in the cellular uptake of macromolecules, in "Peptides, polypeptides and proteins", Proceedings of the Rehovot Symposium on Polyamino acids, polypeptides and proteins and their biological implications, May 1974, Edited by Blout, E. R., Bovey, F. A., Goodman, M. and Lotan, N., J. Wiley and Sons, Inc., New York, pp. 617–628 (1974).

10). Johansson, B. B., "Experimental models of altering the blood-brain barrier", in Progress in Brain Research, Edited by A. Ermisch, R. Landgraf and H. -J. Ruhle, 91: 171–175 (1992)

11). Ermisch, A., "Peptide receptors of the blood-brain barrier and substrate transport into the brain", in Progress in Brain Research, Edited by A. Ermisch, R. Landgraf and H.-J. Ruhle, 91: 155–161 (1992)

12). Schlosshauer, B., "The blood-brain barrier: Morphology, molecules, and neurothelin", BioEssays, 15(5): 341–346 (1993)

13). Bobo R. H., Laske, D. W., Akbasak, A., Morrison, P. F., Dedrick, R. L., and Oldfield, E. H., "Convection-enhanced delivery of macromolecules in the brain", Proc. Natl. Acad. Sci. USA, 91: 2076–2080 (1994).

14). Ommaya, A. K., "Implantable devices for chronic access and drug delivery to the central nervous system", Cancer Drug Delivery, 1(2): 169–178 (1984).

15). Broadwell, R. D., "Transcytosis of macromolecules through the blood-brain barrier: a cell biological perspective and critical appraisal", Acta Neuropathol., 79:117–128 (1989).

16) Moore, S. A., Yoder, E., Murphy, S., Dutton, G. R. and Spector, A. A., "Astrocytes, not neurons, produce docosahexaenoic acid (22:6 omega-3) and arachidonic acid (20:4 omega-6)", J. Neurochem., 56(2), 518–524 (1991).

17) Yerram, N. R., Moore, S. A., and Spector, A. A., "Eicosapentaenoic acid metabolism in brain microvessel endothelium: effect on prostaglandin formation", J. Lipid Research, 30: 1747–1757 (1989).

18) Moore, S. A., Yoder, E., and Spector, A. A., "Role of the blood-brain barrier in the formation of long-chain omega-3 and omega-6 fatty acids from essential fatty acid precursors", J. Neurochem., 55(2): 391–402 (1990).

19) Dobrenis, K., Joseph, A. and Rattazzi, M. C., "Neuronal lysosomal enzyme replacement using fragment C of tetanus toxin", Proc. Natl. Acad. Sci., USA, 89:2297–2301 (1992).

20) Halpern, J. L., and Loftus, A., "Characterization of the receptor-binding domain of tetanus toxin", J. Biol. Chem., 268 (15): 11188–11192 (1993).

We claim:

1. A method for the delivery of biologically active agents to a mammalian brain which method comprises administering to a mammal an effective amount of a biomolecular complex comprising: a) a lipophilic polycationic carrier selected from a group consisting of poly-lysine, poly-arginine and poly-ornithine, wherein said lipophilic polycationic carrier has 2–20 eicosapentaenoic acid moieties attached, b) a biologically active agent, and c) one or more additional eicosapentaenoic acid moieties.

2. The method of claim 1 wherein said lipophilic polycationic carrier has 5 to 50 amino acid residues.

3. The method of claim 2 wherein said lipophilic polycationic carrier has 10 to 25 amino acid residues.

4. The method of claim 1 wherein the one or more additional eicosapentaenoic acid moieties are selected from the group consisting of eicosapentaenoic acid-containing phosphatidyl serine, eicosapentaenoic acid-containing phosphatidyl ethanolamine and eicosapentaenoic acid-containing phosphatidyl carnitine.

5. The method of claim 4 wherein said complex further comprises a targeting moiety selected from the group consisting of the C fragment of tetanus toxin, alpha-bungarotoxin and nerve growth factor.

6. The method of claim 5 wherein said administering is selected from the group consisting of intrathecal injection, surgical implant, direct interstitial infusion into the brain, intravenous and oral administration.

7. A method for the delivery of biologically active agents to a mammalian brain which method comprises administering to a mammal an effective amount of a biomolecular complex comprising: a) a lipophilic polycationic carrier selected from a group consisting of poly-lysine, poly-arginine and poly-ornithine, wherein said polycationic carrier has 2–20 docosahexaenoic acid moieties attached b) a biologically active agent, and c) one or more additional docosahexaenoic acid moieties.

8. The method of claim 7 wherein said lipophilic polycationic carrier has 5 to 50 amino acid residues.

9. The method of claim 8 wherein said lipophilic polycationic carrier has 10 to 25 amino acid residues.

10. The method of claim 7 wherein the one or more additional docosahexaenoic acid moieties are selected from the group consisting of docosahexaenoic acid-containing phosphatidyl serine, docosahexaenoic acid-containing phosphatidyl ethanolamine and docosahexaenoic acid-containing phosphatidyl carnitine.

11. The method of claim 10 wherein said complex further comprises a targeting moiety selected from the group consisting of the C fragment of tetanus toxin, alpha-bungarotoxin and nerve growth factor.

12. The method of claim 11 wherein said administering is selected from the group consisting of intrathecal injection, surgical implant, direct interstitial infusion into the brain, intravenous and oral administration.

13. The method according to claims 1 or 7 wherein said biologically active agent is selected from the group consisting of peptides, polypeptides, proteins, polyethylene glycol-derivatized proteins, enzymes, hormones, growth factors, antigens and antibodies.

14. The method according to claims 1 or 7 wherein said administering is selected from the group consisting of intrathecal injection, surgical implant, direct interstitial infusion into the brain, intravenous administration and oral administration.

15. The method according to claims 1 or 7 wherein said biologically active agent is selected from the group consisting of drugs and diagnostic agents.

16. The method according to claims 1 or 7 wherein said biologically active agent is selected from the group consisting of nucleic acids, oligonucleotides and transfection vectors.

17. The method of claims 4 or 10 wherein said administering is selected from the group consisting of intrathecal injection, surgical implant, direct interstitial infusion into the brain, intravenous and oral administration.

* * * * *